United States Patent
Krueger

(10) Patent No.: US 7,843,201 B2
(45) Date of Patent: Nov. 30, 2010

(54) METHOD OF TESTING LIGHT METAL PARTS, IN PARTICULAR ALUMINUM COMPONENTS, WHICH HAVE BEEN COATED BY ANODISING, IN PARTICULAR BY TSA ANODISING

(75) Inventor: Juergen Krueger, Bremen (DE)

(73) Assignee: Airbus Deutschland GmbH, Hamburg (DE)

( * ) Notice: Subject to any disclaimer, the term of this patent is extended or adjusted under 35 U.S.C. 154(b) by 445 days.

(21) Appl. No.: 11/983,898

(22) Filed: Nov. 13, 2007

(65) Prior Publication Data

US 2008/0122459 A1  May 29, 2008

(30) Foreign Application Priority Data

Nov. 10, 2006   (DE) .................... 10 2006 052 984

(51) Int. Cl.
*G01R 27/08* (2006.01)
*C25D 5/00* (2006.01)
(52) U.S. Cl. .................... 324/693; 205/171
(58) Field of Classification Search ........... 324/693; 205/171
See application file for complete search history.

(56) References Cited

U.S. PATENT DOCUMENTS

| | | | | |
|---|---|---|---|---|
| 4,310,586 A | * | 1/1982 | Sheasby et al. | 428/220 |
| 4,806,849 A | * | 2/1989 | Kihira et al. | 324/700 |
| 6,054,038 A | * | 4/2000 | Davis et al. | 205/776.5 |
| 6,369,589 B1 | * | 4/2002 | Gao et al. | 324/693 |
| 6,446,578 B1 | * | 9/2002 | Irwin | 119/604 |
| 7,339,383 B2 | * | 3/2008 | Konno et al. | 324/662 |

FOREIGN PATENT DOCUMENTS

| | | |
|---|---|---|
| DE | 10235124 | 2/2004 |
| DE | 10 2004 054856 | 5/2006 |
| FR | 2444279 | 7/1980 |

OTHER PUBLICATIONS

German Office Action dated Jul. 22, 2008.

* cited by examiner

*Primary Examiner*—Jeff Natalini
(74) *Attorney, Agent, or Firm*—Jenkins, Wilson, Taylor & Hunt, P.A.

(57) ABSTRACT

A method of testing light metal parts, in particular aluminum components, which have been coated by anodizing, in particular by TSA anodizing, to determine whether they have been coated is described. According to the invention, the surface resistance of the surface of the component is measured and the surface coating of the component is classed as good when the surface resistance is higher than a prescribed high resistance value.

16 Claims, 2 Drawing Sheets a)

b)

METHOD OF TESTING LIGHT METAL PARTS, IN PARTICULAR ALUMINUM COMPONENTS, WHICH HAVE BEEN COATED BY ANODISING, IN PARTICULAR BY TSA ANODISING

CROSS-REFERENCE TO RELATED APPLICATIONS

This application claims the benefit of German Patent Application No. 10 2006 052 984.7, filed Nov. 10, 2006, the entire disclosure of which is herein incorporated by reference.

FIELD OF THE INVENTION

The invention relates to a method of testing light metal parts, in particular aluminum components, which have been coated by anodising, in particular by TSA anodising.

BACKGROUND OF THE INVENTION

Components made of light metal, in particular aluminum alloys, are provided with surface protection by anodising, often also referred to as eloxing, in order to make them resistant to chemical influences. A known standard process for this is chromic acid anodising (CAA). In the production of aircraft, a large number of small sheet metal parts, for example from 10 000 to 14 000 per day, are treated by chromic acid anodising. To carry out anodising, the parts are held in support frames by means of clamps in batches of, for example, up to 800 and dipped simultaneously into appropriate electrochemical baths. Since the components have to be provided with electrical contacts and have a voltage applied to them in order to be anodised, it can happen that individual parts are not anodised or incorrectly anodised because of contact problems. This can be the case for, for example, 0.1% of the parts. Since parts which have not been anodised do not represent the desired in-specification state, these have to be recognized. The recognition of unanodised parts does not represent a problem in the case of the abovementioned chromic acid anodising since anodised parts have a "grey" appearance while unanodised parts have a "bright" appearance.

Since chromic acid anodising is problematical in terms of its environmental acceptability, alternative anodising processes are desirable. The so-called TSA process (TSA=tartaric sulphuric acid) is such an alternative anodising process. As regards the corrosion protection to be provided, the TSA process is at least as good as the above-described CAA process, but the anodised layer cannot be detected by means of simple visual inspection. The visual inspection to be employed in a simple manner for the CAA process can thus not be employed for the more environmentally friendly TSA process to detect unanodised parts.

SUMMARY OF THE INVENTION

It is an object of the invention to provide a method of testing light metal parts, in particular aluminum components, which have been coated by anodising, in particular by TSA anodising, which is simple to employ and can be carried out in a short test time.

According to the invention, the object is achieved by a method having the features of claim 1. Advantageous embodiments and further developments of the method of the invention are indicated in the subordinate claims.

The invention provides a method of testing light metal components, in particular aluminum components, which have been coated by anodising, in particular by TSA anodising, to determine whether they have been coated. According to the invention, the surface resistance of the surface of the component is measured and the surface coating of the component is classed as good when the surface resistance is higher than a prescribed high resistance value.

In an embodiment of the invention, the surface resistance is measured by means of detachable electrodes placed on the surface of the component.

In an embodiment of the invention, the surface resistance between two detachable electrodes placed a distance apart on the surface of the component is measured.

In another embodiment of the method of the invention, the surface resistance between a holding clamp which holds the component for anodising and a detachable electrode placed on the surface of the component at a particular distance from the clamp is measured.

According to a further embodiment of the method of the invention, correct coupling of the detachable electrodes to the component is verified.

In an embodiment of the invention, correct coupling of the detachable electrodes to the component is verified by measuring the contact pressure of the detachable electrodes on the component.

In an embodiment of the invention, the detachable electrodes are placed on the component from the same side.

As an alternative, the detachable electrodes can be placed on the component from opposite sides.

In still another embodiment of the invention, a first detachable electrode is placed on the component from a first side and a second detachable electrode is placed on the component from a second side transverse thereto.

In an embodiment of the invention, the measurement time is less than 0.5 second.

In a further embodiment of the invention, the measurement time is less than 0.3 second.

In an embodiment of the invention, a large number of parts are measured in a cyclically repeating procedure.

In one embodiment, the cyclically repeating procedure comprises taking the anodised component from a support frame which holds the component for anodising and measuring the surface resistance to test the coating and the cycle time of the cyclically repeating procedure is preferably less than 0.5 second, preferably less than 0.3 second.

The cyclically repeating procedure can comprise simultaneous parallel removal from the frame and/or measurement of a plurality of parts.

Finally, the method can be carried out automatically for a large number of identical or similar components.

Examples of the method of the invention are illustrated below with the aid of the drawing.

DETAILED DESCRIPTION OF THE INVENTION

Figure 1:
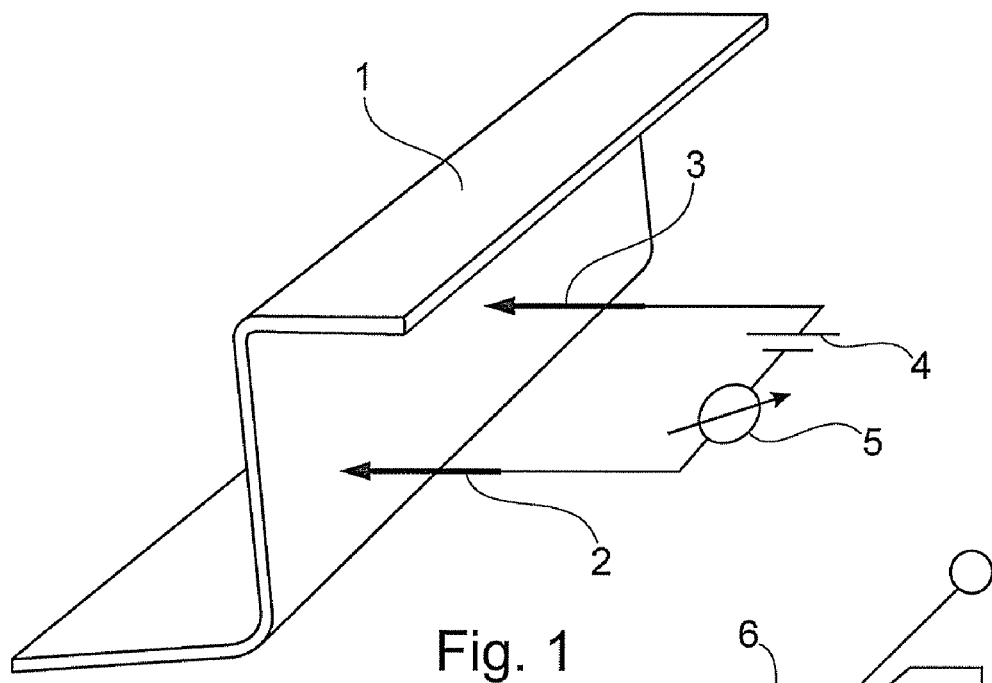
FIG. 1 depicts a schematic perspective view which shows how a component coated by anodising is tested to assess the quality of the coating.
Figure 2:
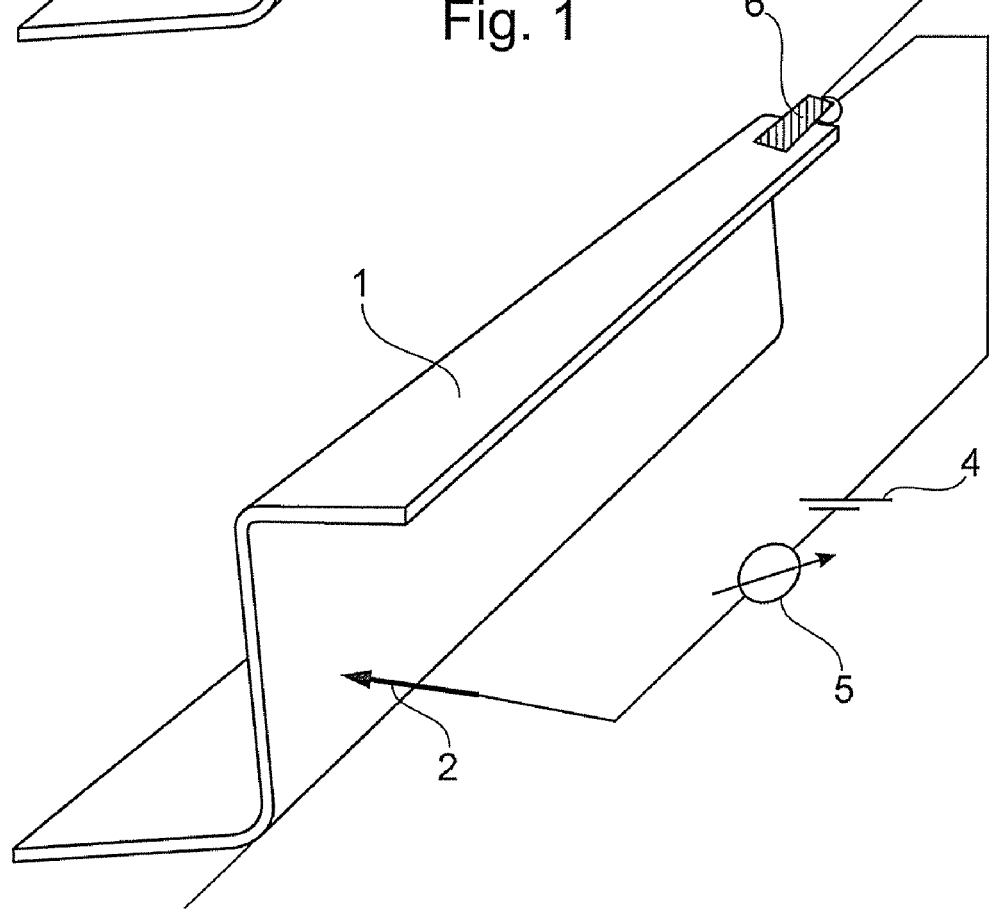
FIG. 2 depicts a schematic perspective view similar to FIG. 1 which shows such testing according to a second example of the invention.

FIGS. 1 and 2 each show a component 1 which can be produced from light metal, in particular an aluminum alloy. The component can be one of many identical or similar components manufactured in large numbers, in particular components as are used in aircraft construction. To provide surface protection, a coating is produced on the surface of the component 1 by anodising (eloxing). In the schematic enlarged cross-sectional view of FIG. 3a), this coating 8 is depicted in an overproportional thickness.

To test whether the coating or anodised layer 8 is present correctly on the component 1, the surface resistance of the surface of the component 1 is measured and the surface coating 8 is classed as good when the surface resistance is higher than a prescribed high resistance value (or the conductivity value is lower than a prescribed low conductivity value).

The surface resistance is quite generally measured by establishing electrical contact with the component 1 at two places some distance apart on the component and connecting these places with one another by means of an electrical measurement arrangement, as depicted in simplified form as a current source 4 and a current measuring instrument 5 in FIGS. 1 and 2. In the case of a part 1 having an anodised layer 8 which is correctly present, the resistance is in the region of some megaohm, which in the case of measurement using simple universal measuring instruments is indicated by an "infinite" resistance, while in the case of a part 1 without an anodised layer, the resistance is substantially lower in the range from, for example, 0.2 to 2 ohm. In the case of a layer 8 which has been formed only partly or poorly, the resistance could be in a higher but still finite resistance range.

The surface resistance of the component 1 is, according to the example depicted, measured by means of detachable electrodes 2, 3 coupled to the component at the surface 7a, 7b.

In the example shown in FIG. 1, the surface resistance between two electrodes 2, 3 placed a distance apart on the surface 7a, 7b of the component 1 is measured.

In the example shown in FIG. 2, the surface resistance between a holding clamp 6 which holds the component for anodising and an electrode 2 placed some distance away on the surface 7a, 7b of the component 1 is measured.

Figure 3:
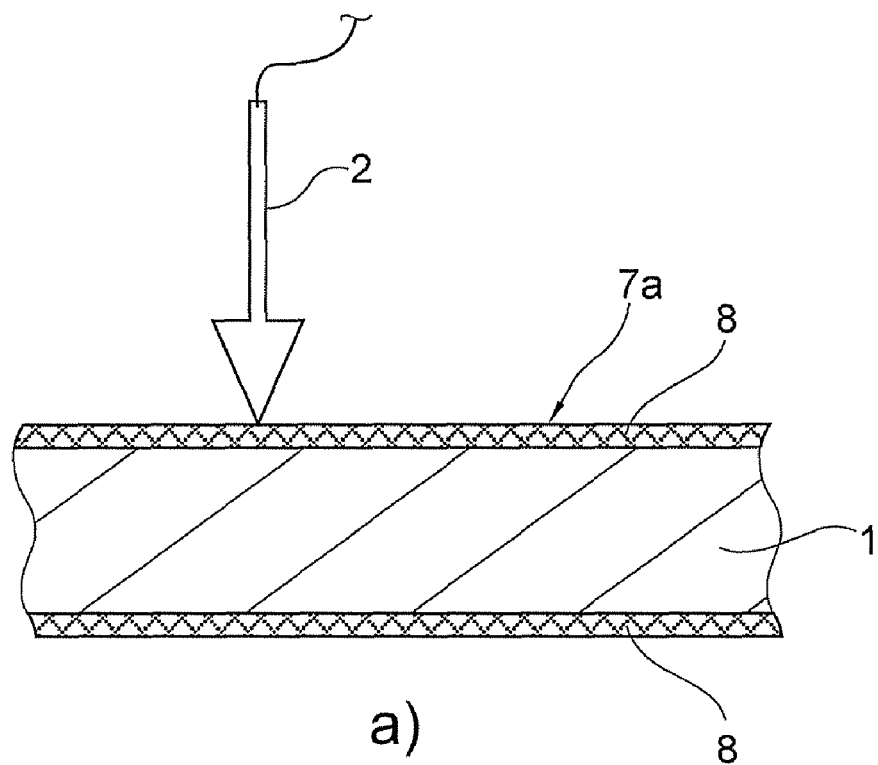
FIGS. 3a) and b) each show enlarged schematic cross-sectional views of a component which is being tested in respect of its coating, in the case a) a coating which is correctly present and in case b) an absent coating.
Figure 3:
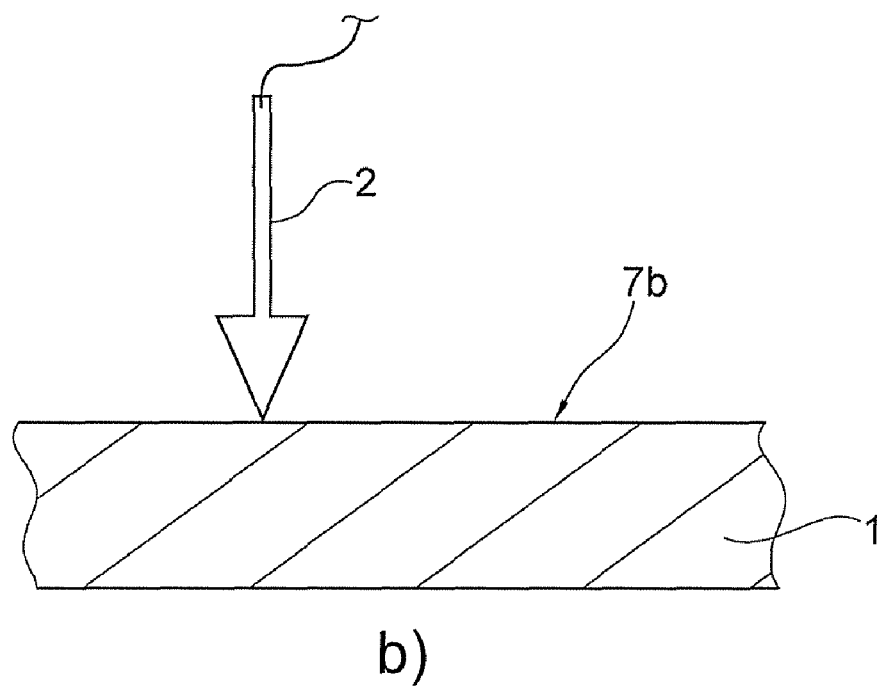

As shown by FIG. 3, in which a detachable electrode 2 is shown firstly for the case of an anodised layer 8 which is correctly present, FIG. 3a), and secondly for the case of an absent anodised layer, FIG. 3b), there is in the first case the anodised layer 8 having a high resistance between the electrode 2 and the component 1, so that the measured resistance is high, while this layer is absent in the other case, so that the measured resistance is low.

Correct coupling of the detachable electrodes 2, 3 to the component 1 is preferably verified since in the case of incorrect coupling of one or more of the detachable electrodes 2, 3 a high "infinite" resistance similar to the case of a correct anodised layer 8 can be measured, so that these two cases cannot be distinguished reliably. Correct coupling of the electrodes 2, 3 to the component 1 can be verified by, for example, measuring the contact pressure of the electrodes 2, 3 on the component 1. The measurement can be released as valid only when the presence of a sufficiently high contact pressure has been established.

The detachable electrodes 2, 3 can be placed on the component 1 from the same side or else from opposite sides. Furthermore, a first detachable electrode 2 could be placed on the component from a first side and a second detachable electrode 3 could be placed on the component from a second side transverse thereto, for example at right angles thereto.

The test method is particularly suitable for testing large numbers of identical parts, parts of the same type or similar parts, as are used, for example, in aircraft construction. For this purpose, the test method should be simple to employ and the test time should be very short. The importance of short measurement times is made clear by the fact that in the case of the manufacture of, for example, 14 000 parts per day and an assumed test time of 1 second per component, testing of a day's production would take about four hours. It is therefore advantageous for the measurement time to be less than 0.5 second, preferably less than 0.3 second.

According to the invention, a large number of parts can be measured in a cyclically repeating procedure. The cyclically repeating procedure can comprise taking the anodised component 1 from a support frame which holds the component 1 for anodising together with many other such components and measuring the surface resistance to test the coating 8. The cycle time of the cyclically repeating procedure can preferably be less than 0.5 second, preferably less than 0.3 second. The cyclically repeating procedure can comprise simultaneous parallel removal of a number of parts 1 from the frame and/or measurement of these in respect of their surface coating 8. The method could also be carried out automatically for a large number of identical components 1, components 1 of the same type or similar components 1.

A significant advantage of the method of the invention is that components which have been coated by the environmentally friendly TSA process can be tested for correct coating simply, quickly and reliably, which is not possible by means of visual examination.

What is claimed is:

1. A method of testing coated light metal parts, to determine whether they have been coated, comprising the steps:
    providing a coating on a surface of the light metal part by anodising;
    measuring surface resistance of the surface of the light metal part;
    classifying the surface coating of the surface of the light metal part as good when the measured surface resistance is higher than a prescribed high resistance value, wherein the surface resistance is measured by detachable electrodes placed on the surface of the light metal part and wherein correct coupling of the detachable electrodes to the light metal part is verified.

2. The method according to claim 1, wherein the surface resistance between two detachable electrodes placed a distance apart on the surface of the light metal part is measured.

3. The method according to claim 2, wherein the detachable electrodes are placed on the light metal part from the same side.

4. The method according to claim 2, wherein the detachable electrodes are placed on the light metal part from opposite sides.

5. The method according to claim 2, wherein a first detachable electrode is placed on the light metal part from a first side and a second detachable electrode is placed on the light metal part from a second side transverse thereto.

6. The method according to claim 1, wherein the surface resistance between a holding clamp which holds the light metal part for anodising and a first detachable electrode is measured, wherein the first detachable electrode is placed on the surface of the light metal part at a particular distance from the holding clamp.

7. The method according to claim 1, wherein correct coupling of the detachable electrodes to the component is verified by measuring the contact pressure of the detachable electrodes on the component.

8. The method according to claim 1, wherein the measurement time is less than 0.5 second.

9. The method according to claim 1, wherein the measurement time is less than 0.3 second.

10. The method according to claim 1, wherein a large number of parts are measured in a cyclically repeating procedure.

11. The method according to claim 10, wherein the cyclically repeating procedure comprises taking an anodised light metal part from a support frame which holds the light metal part for anodising and measuring the surface resistance to test the coating and wherein the cycle time of the cyclically repeating procedure is less than 0.5 second.

12. The method according to claim 11, wherein the method of the cyclically repeating procedure comprises simultaneous removal from the support frame and/or simultaneous measurement of a plurality of anodised light metal parts.

13. The method according to claim 10, wherein the cycle time of the cyclically repeating procedure is less than 0.3 second.

14. The method according to claim 1, wherein the method is carried out automatically for a large number of identical or similar light metal parts.

15. The method according to claim 1, wherein the light metal parts are aluminum components.

16. The method according to claim 1, wherein the light metal parts have been anodised by tartaric sulphuric acid (TSA) anodising.

* * * * *